US012653682B2

(12) United States Patent
Sansur et al.

(10) Patent No.: US 12,653,682 B2
(45) Date of Patent: Jun. 16, 2026

(54) DEVICE AND METHOD FOR SACROILIAC FUSION

(71) Applicant: University of Maryland, Baltimore, Baltimore, MD (US)

(72) Inventors: Charles Sansur, Annapolis, MD (US); Steven C. Ludwig, Baltimore, MD (US); Ryan Smith, College Park, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 537 days.

(21) Appl. No.: 18/182,495

(22) Filed: Mar. 13, 2023

(65) Prior Publication Data

US 2023/0285156 A1     Sep. 14, 2023

Related U.S. Application Data

(60) Provisional application No. 63/328,449, filed on Apr. 7, 2022, provisional application No. 63/318,817, filed on Mar. 11, 2022.

(51) Int. Cl.
A61F 2/30 (2006.01)
A61B 17/70 (2006.01)
A61B 17/86 (2006.01)

(52) U.S. Cl.
CPC ...... A61F 2/30988 (2013.01); A61B 17/7055 (2013.01); A61F 2002/30995 (2013.01)

(58) Field of Classification Search
CPC ............ A61F 2002/30995; A61F 2/446; A61F 2/4465; A61B 17/7055; A61B 17/8685; A61B 17/863
See application file for complete search history.

(56) References Cited

U.S. PATENT DOCUMENTS 4,456,005 A * 6/1984 Lichty ................ A61B 17/8685
                                            606/328
4,640,271 A * 2/1987 Lower ................ A61B 17/8685
                                            606/328

(Continued)

FOREIGN PATENT DOCUMENTS

EP        3 315 085 A1     5/2018
EP        3 744 273 A1    12/2020

(Continued)

OTHER PUBLICATIONS

European Search Report issued in copending European Patent Application No. 23190703.1 on May 8, 2024.

*Primary Examiner* — Zade Coley
(74) *Attorney, Agent, or Firm* — Whiteford, Taylor & Preston, LLP

(57)          ABSTRACT

An implantable device for sacroiliac ("SI") joint fusion and an associated method employ an SI joint fusion portion and an anchor portion of smaller diameter than the SI joint fusion portion and that extends distally from a distal end of the SI joint fusion portion. The SI joint fusion portion is externally threaded and is configured to, when surgically implanted, extend across the SI joint. The anchor portion in turn extends distally from the SI joint fusion portion and is configured for implanting entirely within the patient's ilium adjacent the SI joint. In certain configurations, the joint fusion portion is configured to enable fixation of spinal equipment at a proximal end of the joint fusion portion.

9 Claims, 6 Drawing Sheets

(56) References Cited

U.S. PATENT DOCUMENTS

| | | | | |
|---|---|---|---|---|
| 5,334,205 | A * | 8/1994 | Cain | A61B 17/1742 |
| | | | | 606/86 R |
| 5,498,265 | A * | 3/1996 | Asnis | A61B 17/74 |
| | | | | 606/53 |
| 5,562,371 | A * | 10/1996 | Reed | B23G 5/062 |
| | | | | 408/222 |
| 5,645,598 | A * | 7/1997 | Brosnahan, III | A61F 2/446 |
| | | | | 623/17.11 |
| 5,827,285 | A * | 10/1998 | Bramlet | A61B 17/80 |
| | | | | 606/328 |
| 6,471,707 | B1 * | 10/2002 | Miller | A61B 17/8883 |
| | | | | 606/77 |
| 6,921,403 | B2 * | 7/2005 | Cragg | A61B 17/7098 |
| | | | | 606/279 |
| 7,192,446 | B2 * | 3/2007 | Shapiro | A61F 2/446 |
| | | | | 623/17.11 |
| 7,261,716 | B2 * | 8/2007 | Strobel | A61B 17/8625 |
| | | | | 606/232 |
| 7,582,107 | B2 * | 9/2009 | Trail | A61B 17/8685 |
| | | | | 606/916 |
| 7,708,766 | B2 * | 5/2010 | Anderson | A61B 17/863 |
| | | | | 606/301 |
| 8,317,825 | B2 * | 11/2012 | Stone | A61F 2/0805 |
| | | | | 604/93.01 |
| 8,562,651 | B2 | 10/2013 | Metcalf et al. | |
| 8,747,472 | B2 * | 6/2014 | Ainsworth | A61B 17/7014 |
| | | | | 606/328 |
| 8,814,867 | B2 * | 8/2014 | Anderson | A61B 17/1617 |
| | | | | 606/63 |
| 9,119,732 | B2 * | 9/2015 | Schifano | A61B 17/7055 |
| 9,358,057 | B1 | 6/2016 | Whipple et al. | |
| 9,636,230 | B2 * | 5/2017 | Talwar | A61B 17/1757 |
| 9,717,538 | B2 | 8/2017 | Chin et al. | |
| 9,770,277 | B2 * | 9/2017 | Biedermann | A61B 17/864 |
| 9,872,712 | B2 * | 1/2018 | Trieu | A61B 17/8665 |
| 9,931,141 | B2 | 4/2018 | Jimenez | |
| 10,064,669 | B2 * | 9/2018 | Garvey | A61B 17/8685 |
| 10,117,693 | B2 * | 11/2018 | Ehler | A61B 17/7055 |
| 10,932,838 | B2 * | 3/2021 | Mehl | A61B 17/8685 |
| 11,083,511 | B2 | 8/2021 | Schifano et al. | |
| 11,197,704 | B2 * | 12/2021 | Gault | A61B 17/68 |
| 11,234,830 | B2 | 2/2022 | Mesiwala et al. | |
| 11,369,419 | B2 | 6/2022 | Mesiwala et al. | |
| 11,553,953 | B1 | 1/2023 | Robbins | |
| 11,603,203 | B2 | 3/2023 | Fenny et al. | |
| 11,672,570 | B2 | 6/2023 | Stuart et al. | |
| 11,672,664 | B2 | 6/2023 | Mauldin et al. | |
| 11,678,997 | B2 | 6/2023 | Mesiwala et al. | |
| 11,684,378 | B2 | 6/2023 | Reiley et al. | |
| 11,752,011 | B2 | 9/2023 | Stuart et al. | |

| | | | | |
|---|---|---|---|---|
| 12,076,251 | B2 | 9/2024 | Mesiwala et al. | |
| 2002/0133156 | A1 * | 9/2002 | Cole | A61B 17/725 |
| | | | | 606/62 |
| 2003/0018389 | A1 * | 1/2003 | Castro | A61B 17/1757 |
| | | | | 606/90 |
| 2004/0210227 | A1 * | 10/2004 | Trail | A61B 17/8635 |
| | | | | 606/328 |
| 2004/0230195 | A1 * | 11/2004 | Kaikkonen | A61B 17/8635 |
| | | | | 606/317 |
| 2005/0143735 | A1 * | 6/2005 | Kyle | A61B 17/8685 |
| | | | | 606/60 |
| 2009/0326533 | A1 * | 12/2009 | Dell'Oca | A61B 17/8645 |
| | | | | 606/64 |
| 2011/0060373 | A1 * | 3/2011 | Russell | A61B 17/0401 |
| | | | | 606/86 R |
| 2011/0190830 | A1 * | 8/2011 | Biedermann | A61B 17/864 |
| | | | | 606/305 |
| 2012/0191191 | A1 * | 7/2012 | Trieu | A61B 17/864 |
| | | | | 623/17.11 |
| 2013/0090699 | A1 * | 4/2013 | Holzwarth | A61B 17/1637 |
| | | | | 606/309 |
| 2013/0238036 | A1 * | 9/2013 | Sinha | A61B 17/68 |
| | | | | 606/317 |
| 2013/0261671 | A1 * | 10/2013 | Horvath | A61C 8/0006 |
| | | | | 606/306 |
| 2013/0338722 | A1 * | 12/2013 | Yalizis | A61B 17/68 |
| | | | | 606/312 |
| 2014/0031934 | A1 * | 1/2014 | Trieu | A61B 17/8685 |
| | | | | 623/17.11 |
| 2014/0074175 | A1 * | 3/2014 | Ehler | A61B 17/863 |
| | | | | 606/329 |
| 2014/0107781 | A1 * | 4/2014 | Bagga | A61B 17/68 |
| | | | | 623/16.11 |
| 2016/0081719 | A1 * | 3/2016 | Faulhaber | A61B 17/7035 |
| | | | | 606/309 |
| 2016/0242820 | A1 | 8/2016 | Whipple et al. | |
| 2016/0287301 | A1 * | 10/2016 | Mehl | A61B 17/8685 |
| 2016/0310188 | A1 * | 10/2016 | Marino | A61F 2/28 |
| 2016/0317200 | A1 * | 11/2016 | Hoogervorst | A61B 17/921 |
| 2017/0112554 | A1 * | 4/2017 | Zadeh | A61B 17/8685 |
| 2018/0177539 | A1 * | 6/2018 | Ehler | A61B 17/846 |
| 2018/0317989 | A1 * | 11/2018 | Sellers | A61B 17/8685 |
| 2020/0121375 | A1 | 4/2020 | Schifano et al. | |
| 2021/0022873 | A1 | 1/2021 | Patel | |
| 2021/0212734 | A1 | 7/2021 | Mesiwala et al. | |
| 2021/0322057 | A1 * | 10/2021 | Fessler | A61B 17/7001 |
| 2023/0285156 | A1 | 9/2023 | Sansur et al. | |

FOREIGN PATENT DOCUMENTS

| | | | | |
|---|---|---|---|---|
| WO | WO-2006124987 A1 * | 11/2006 | | A61B 17/8685 |
| WO | 2016/122208 A1 | 8/2016 | | |

* cited by examiner

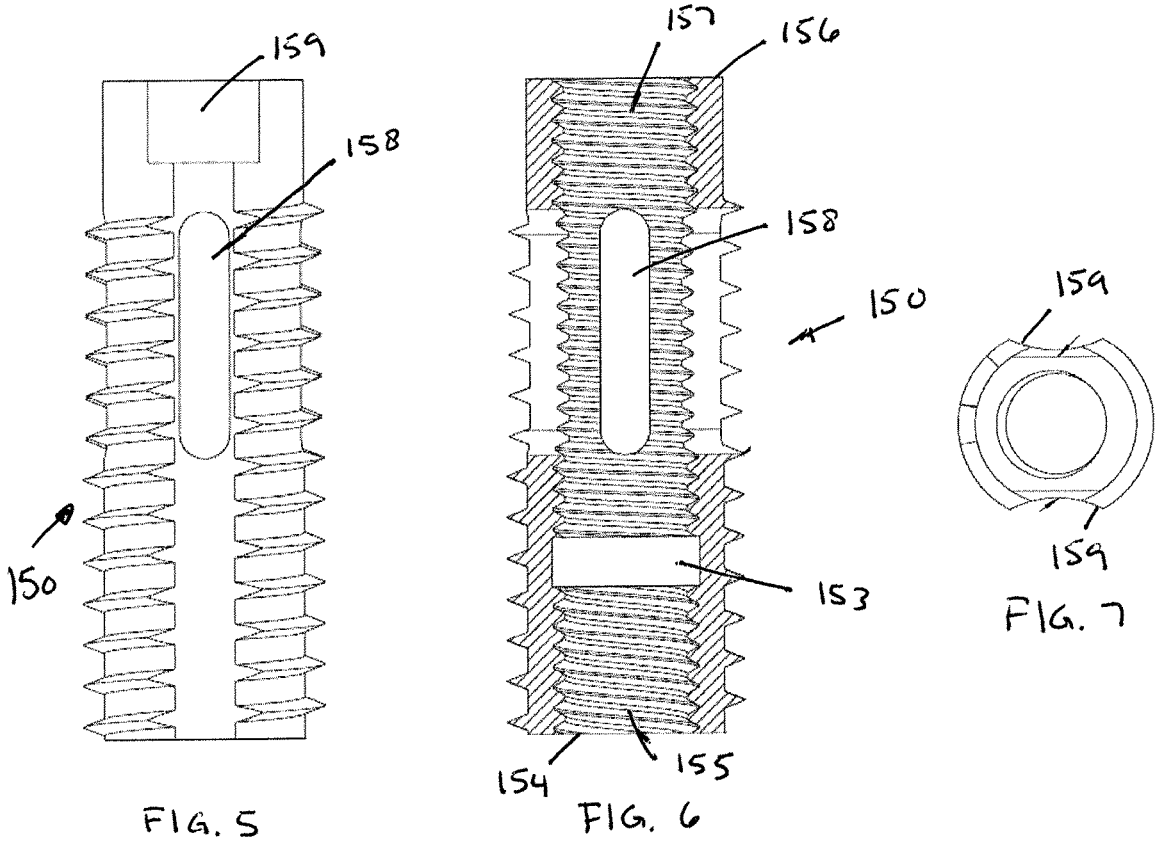
FIG. 5
FIG. 6
FIG. 7
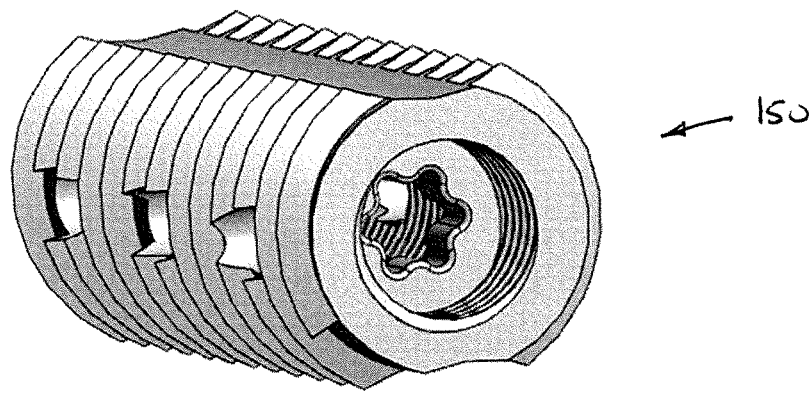
FIG. 8

150

100

110

150     160                          110

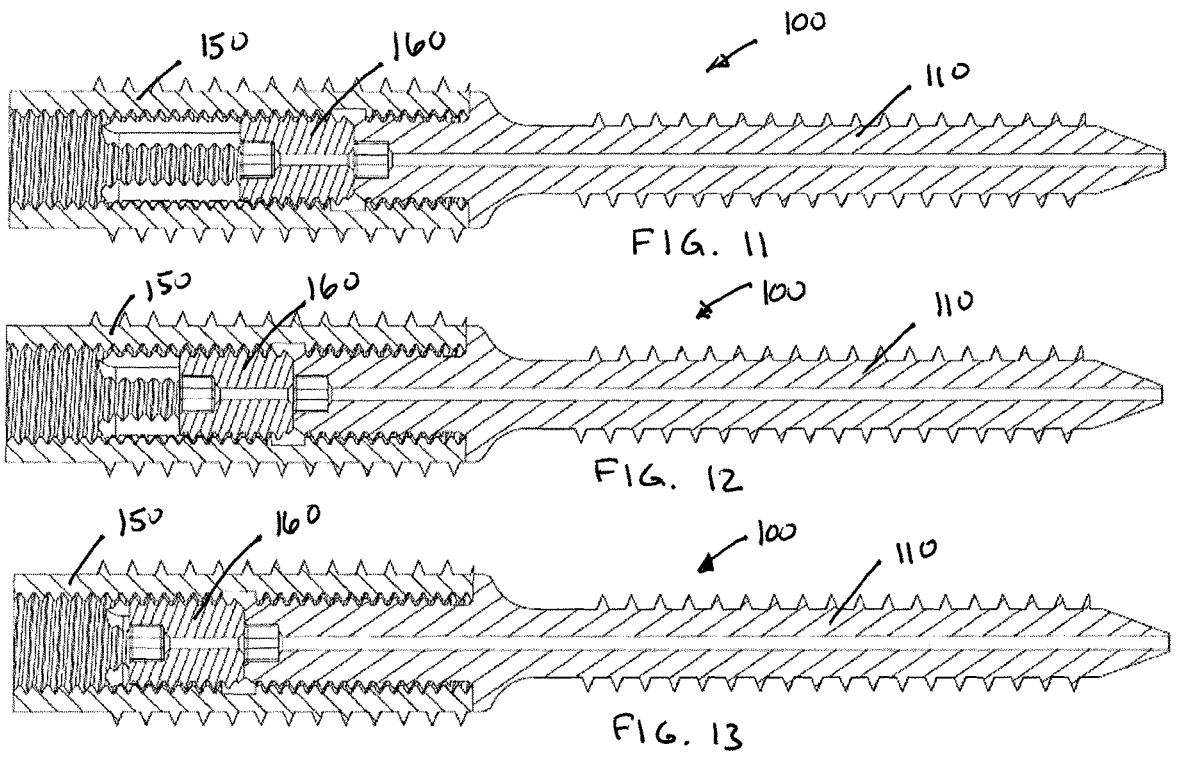
FIG. 11
FIG. 12
FIG. 13
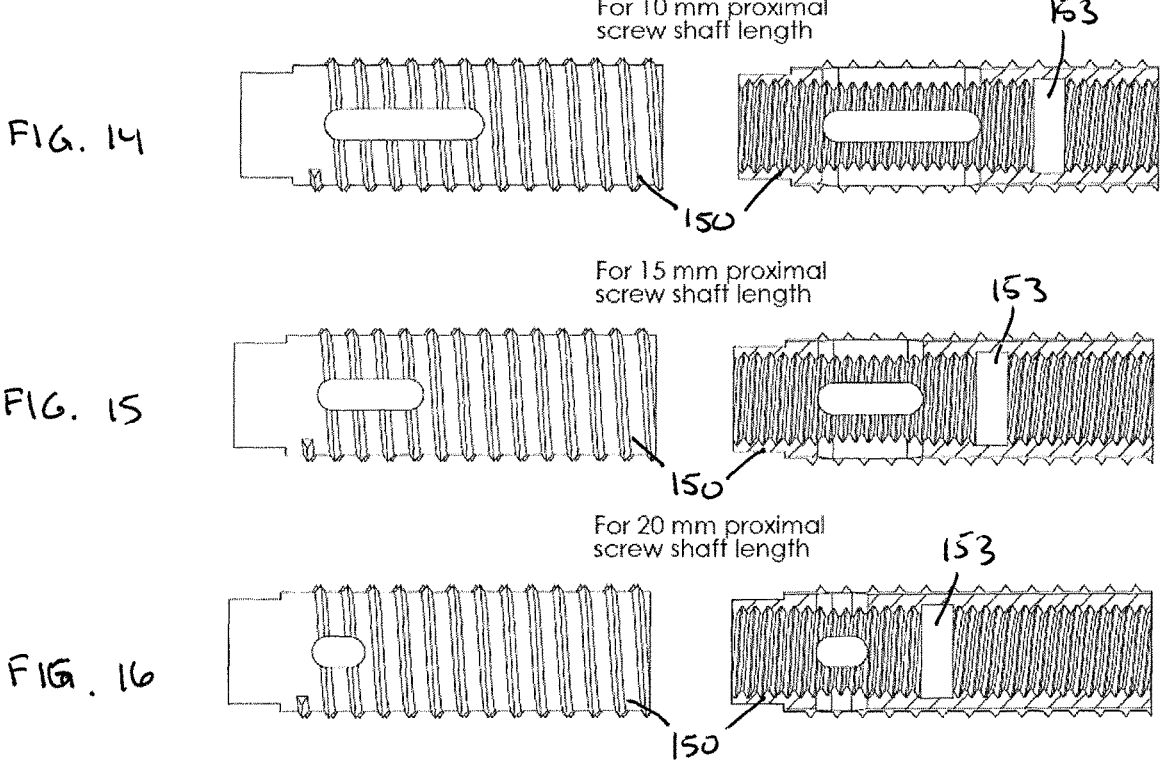
FIG. 14
For 10 mm proximal
screw shaft length
FIG. 15
For 15 mm proximal
screw shaft length
FIG. 16
For 20 mm proximal
screw shaft length

DEVICE AND METHOD FOR SACROILIAC FUSION

CROSS-REFERENCE TO RELATED APPLICATIONS

This application claims the benefit of U.S. Provisional Patent Application No. 63/318,817 titled "DEVICE AND METHOD FOR SACROILIAC FUSION," filed by the inventors herein on Mar. 11, 2022, and of U.S. Provisional Patent Application No. 63/328,449 titled "DEVICE AND METHOD FOR SACROILIAC FUSION," filed by the inventors herein on Apr. 7, 2022, the specifications of which are incorporated herein by reference in their entireties.

FIELD OF THE INVENTION

This invention relates generally to implantable medical devices and methods for joint fusion, and more particularly to a system and method for fusion of a sacroiliac joint.

BACKGROUND

Lower back pain and leg pain have often been found to be attributable to sacroiliac ("SI") joint problems, such as by way of example instability in the SI joint. SI joint fusion is a surgical procedure that in certain instances is thus employed to mitigate back and leg pain. Moreover, SI joint fusion has been employed to treat patients with adjacent segment disease resulting from lumbar fusions. In certain circumstances, patients that require fixation of spinal stabilization equipment to the pelvis in order to augment spinal stability and maintain the intended corrective benefit of such spinal stabilization equipment may experience both pain and hardware failure at the point of attachment to the pelvis, creating a need for improved methods and devices of fixation for such equipment, particularly at the SI joint.

Recently, there has been an emergence of minimally invasive techniques designed for the treatment of the SI joint, such as SI joint fusion to mitigate lower back and leg pain. The surgical procedure typically involves the use of screws to stabilize the SIjoint. However, previously known SI joint stabilization screws have been difficult to install, and have employed configurations that may not be suitable for all patients.

Thus, there remains a need in the art for SI joint stabilization devices and methods that are more easily installed, that may provide both secure fixation of spinal equipment and fusion of the SI joint, and that cause less discomfort to the patient both post-operatively and long term than previously known devices.

SUMMARY OF THE INVENTION

Disclosed are systems and methods for SI joint fusion that avoid one or more disadvantages of previously known systems and methods, and that with respect to certain aspects of an embodiment of the invention provides ease of installation and greater versatility in adapting to individual patient needs.

In accordance with certain aspects of an embodiment of the invention, an implantable device for SI joint fusion and an associated method are provided having an SI joint fusion portion and an anchor portion of smaller diameter than the SI joint fusion portion and that extends distally from a distal end of the SI joint fusion portion. The SI joint fusion portion is externally threaded and is configured to, when surgically implanted, extend across the SI joint. The anchor portion in turn extends distally from the SI joint fusion portion and is configured for implanting entirely within the patient's ilium adjacent the SI joint. In certain configurations, the joint fusion portion is configured to enable fixation of spinal equipment at a proximal end of the joint fusion portion.

In accordance with further aspects of an embodiment of the invention, an implantable modular device for SI joint fusion and an associated method are provided having an SIjoint fusion portion that is threadably attached to an anchor portion of smaller diameter than the SI joint fusion portion and that extends distally from a distal end of the SI joint fusion portion. The SI joint fusion portion is externally threaded and is configured to, when surgically implanted, extend across the SI joint. The anchor portion in turn extends distally from the SI joint fusion portion and is configured for implanting entirely within the patient's ilium adjacent the SI joint. As the implantable device for SI joint fusion is a modular assembly, its components may be installed either together or separately form one another as may best suit the particular operating conditions for a given patient.

In accordance with certain aspects of an embodiment of the invention, a modular system for sacroiliac joint fusion is provided, comprising a joint portion having a first diameter, a joint portion proximal end, a joint portion distal end, a first plurality of joint portion threads on an exterior of the joint portion, and a second plurality of joint portion threads on an interior of the joint portion; and an anchor portion having a second diameter that is less than the first diameter of the joint portion, the anchor portion having an anchor portion proximal end, an anchor portion distal end, a first plurality of anchor portion threads on a distal length of the anchor portion, and a second plurality of anchor portion threads on a proximal length of the anchor portion; wherein the second plurality of anchor portion threads engage with the second plurality of joint portion threads to engage the joint portion to the anchor portion; and wherein a lead of the first plurality of joint portion threads matches a pitch of the first plurality of anchor portion threads. That modular system may be implanted through the steps of: forming a first opening in an iliac bone of a patient having a diameter substantially equal to said second diameter of said anchor portion; forming a second opening in a sacrum of the patient having a diameter substantially equal to the first diameter of the joint portion and extending across an SI joint of the patient and into the iliac bone; inserting the anchor portion into the first opening and inserting the joint portion into the second opening such that the joint portion extends across the SI joint and such that the first plurality of anchor portion threads are disposed entirely within the iliac bone.

In accordance with further aspects of an embodiment of the invention, a device for sacroiliac joint fusion is provided, comprising: a joint portion having a first diameter, a joint portion proximal end and a joint portion distal end, the joint portion configured for implantation across an SI joint of a patient such that the joint portion distal end extends into an ilium of the patient from a sacrum of the patient; and an anchor portion having a second diameter that is less than the first diameter of the joint portion, the anchor portion extending distally from the distal end of the joint portion and configured for implantation into the ilium of the patient such that the entire length of the anchor portion that is distal to the joint portion is implanted within the ilium of the patient. That device may be implanted through the steps of: forming a first opening in the ilium of the patient having a diameter substantially equal to the second diameter of the anchor portion; forming a second opening in the sacrum of the patient having a diameter substantially equal to the first diameter of the joint portion and extending across the SI joint of the patient and into the ilium; inserting the anchor portion into the first opening and inserting the joint portion into the second opening such that the joint portion extends across the SI joint and such that the first plurality of anchor portion threads are disposed entirely within the iliac bone.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

FIG. 5 is a side view of a joint fusion portion of the implantable device of FIG. 1.

FIG. 6 is a side cross-sectional view of the joint fusion portion of FIG. 5.

FIG. 7 is a top view of the joint fusion portion of FIG. 5.

FIG. 8 is a perspective view of the joint fusion portion of FIG. 5.

FIGS. 11-13 are side cross-sectional views of the implantable device of FIG. 1 showing varying lengths of the anchor portion.

FIGS. 14-16 are side views and side cross-sectional view of the joint fusion portion showing varying internal thread configurations to accommodate varying lengths of the anchor portion.

DETAILED DESCRIPTION OF THE PREFERRED EMBODIMENTS

Figures 1, 2, 3, 4:
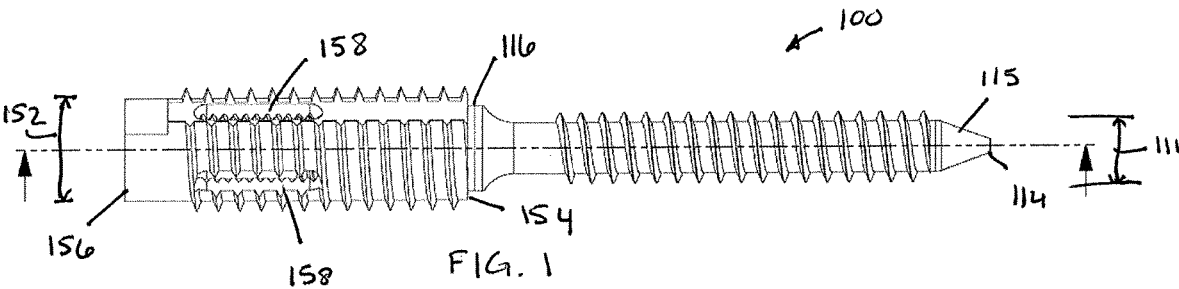
FIG. 1 is a side view of an implantable device for SI joint fusion in accordance with certain aspects of an embodiment of the invention.
FIG. 2 is a side view of an anchor portion of the implantable device of FIG. 1.
FIG. 3 is a side cross-sectional view of the anchor portion of FIG. 2.
FIG. 4 is a top view of the anchor portion of FIG. 2.

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

In accordance with certain aspects of an embodiment, an implantable device and associated method are provided that are adapted to standardize pelvic fixation techniques via open or minimally invasive approaches using SI joint fusion techniques. A device according to aspects of the invention includes an integrated pelvic and SI joint fusion and fixation body that may be configured to integrate with other devices, such as hardware for stabilization of a patient's spinal column. In certain configurations, the device may facilitate simultaneous hardware fixation and fusion through the SI joint. Likewise in certain configurations, the device may be modular, for example, such that separate components of the device (further described below) can be placed individually. Thus, the device and method can streamline the workflow of SI joint fusion techniques. Likewise in certain configurations, the device may be used to convert a previously-placed SI joint fusion device to another technique, such as anchoring of spinal hardware. For example, the device can be configured to convert a previously-placed isolated SI joint fusion screw to a pelvic fixation device for lumbosacral hardware. In accordance with still further aspects of the invention, the device configured in accordance with at least certain aspects of the invention is adapted to facilitate arthrodesis of the SI joint. A device and method configured in accordance with certain aspects of the invention may mitigate pain generated by excessively violating the SI joint, and may provide longer lasting pelvic fixation and SI joint fusion, compared to typical devices and methods. Thus, a device and method configured in accordance with aspects of the invention may reduce the likelihood of hardware-related complications compared to typical devices and methods.

Referring now to FIG. 1 and in accordance with certain aspects of an embodiment, an implantable device 100 for SI joint fusion is provided having an anchor portion 110 and a joint fusion portion 150. The anchor portion 110 is configured to be placed in the iliac portion of a patient's pelvis, and more particularly the patient's iliac bone, to provide fixation of the implantable device 100. For example, the anchor portion 110 may be configured to be placed in a bony portion of the patient's ilium in which the bone is relatively weak. Likewise, joint fusion portion 150 is configured to be placed across the patient's SI joint to fuse the patient's sacrum to the patient' ilium, with the anchor portion extending distally from the joint fusion portion into the patient's ilium.

Anchor portion 110 is a generally cylindrical, elongated member having an anchor portion outer diameter 111, an anchor portion distal end 114, and an anchor portion proximal portion 116. Anchor portion distal end 114 includes a tip 115 configured for insertion into a hole, such as a pilot hole that has been drilled into a patient's ilium in advance of implantation of implantable device 100, or a hole that is formed by direct insertion of the implantable device 100 into the patient's bone, such as by screwing the implantable device 100 into place. In exemplary configurations, tip 115 can have one of a wide variety of shapes, such as conical-like, blunt, or rounded. In certain configurations, tip 115 may be configured to remove material from the hole into which anchor portion 110 is inserted and/or bone from the space into which the anchor portion 110 is inserted. For example, anchor portion 110 may have an internal cannula 117 (FIG. 3) extending longitudinally through anchor portion 110 from anchor portion distal end 114 to and out of anchor portion proximal portion 116 and into a hollow interior of joint fusion portion 150. The proximal portion 116 of anchor portion 110 is joined to joint fusion portion 150 such that anchor portion 110 extends distally from the distal end of joint fusion portion 150.

Joint fusion portion 150 is likewise a generally cylindrical, elongate member having a joint fusion portion outer diameter 152 that is greater than anchor portion outer diameter 111, a joint fusion portion distal end 154, and a joint fusion portion proximal end 156. Joint fusion portion proximal end 156 is open and defines internal threads 157 (FIG. 6) along an interior circumferential wall (discussed in greater detail below), which internal threads are configured to receive other threaded equipment and/or accessories, such as by way of non-limiting example a threaded polyaxial tulip head (having a construction well known to those of ordinary skill in the art) configured for connecting a rod extending from spinal fixation equipment so as to enable fixation of such spinal equipment to joint fusion portion 150. Joint fusion portion 150 also preferably includes a plurality of slots 158 extending through the outer wall of joint fusion portion 150 into the hollow interior of joint fusion portion 150 in order to promote bone growth into joint fusion portion 150, further aiding in fusion of the patient's SI joint. In an exemplary configuration, joint fusion portion 150 has a generally cylindrical shape, but may likewise employ an elliptical-like cross-section, such as oval, although those skilled in the art will recognize that other cross-sectional configurations may be provided to meet the needs and/or preferences of an operator.

In certain exemplary configurations, anchor portion 110 and joint fusion portion 150 are formed integrally as a single unit. In other configurations and with particular reference to FIGS. 2-7, anchor portion 110 is a separate component from joint fusion portion 150, such that implantable device 100 is a modular system of components that may be installed independently of one another. In such modular assembly, anchor portion 110 and joint fusion portion 150 are configured to mechanically couple to one another, as further detailed below. For example, proximal portion 116 of anchor portion 110 may include a threaded head 118 enabling attachment of anchor portion 110 to the joint fusion portion distal end 154 via internal threads 155 at the joint fusion portion distal end 154. As particularly shown in FIG. 6, an internal, smooth cylindrical wall defines a gap 153 between internal threads 155 at joint fusion portion distal end 154 and internal threads 157 extending from the proximal end of joint fusion portion 150 to separate the differing connecting thread regions (with the distal edge of the gap being positioned to coincide with the end of proximal portion 116 of anchor portion 110 when fully attached to joint fusion portion 150).

In accordance with certain aspects of an embodiment, anchor portion 110 is configured to be inserted into bone, such as the iliac bone of a patient's pelvis, by screwing or forcing, such that the anchor portion 110 is substantially entirely positioned with the patient's iliac bone to ensure sufficient anchoring of the device 100. For example, anchor portion 110 may have a length that is approximately equal to or less than a hole formed in advance in the patient's iliac bone in which anchor portion 110 is to be placed. As a result, anchor portion 110 is less likely to fail due to fatigue strains, particularly in comparison to typical devices, because it is particularly configured to not bridge the patient's SI joint (i.e., anchor portion 110 is configured to experience fewer bending fatigue stresses across the SI joint compared to typical devices) when placed in the patient's pelvis. In certain configurations, anchor portion 110 is inserted posteriorly into the patient's iliac bone using a medial to lateral trajectory.

In exemplary configurations, anchor portion 110 provides fixation in at least one of multiple ways, such as by way of non-limiting example, through mechanical fixation, friction-fitting, encouraging bone in-growth, and the like. In accordance with certain aspects of the invention, anchor portion 110 is provided external threads 112 on its external surface that are adapted to function as bone threads for mechanical fixation of the anchor portion 110 to the patient's iliac bone. The external threads 112 are generally configured for fixation in weak bone (e.g., iliac portion of the pelvis). Thus, threads 112 may have properties, such as a pitch, depth, cross-sectional shape, etc. that increase fixation of anchor portion 110 in weak bone. In a particular exemplary embodiment, threads 112 may comprise M8×1.0 triple-start thread paired with 3.0 mm pitch bone thread. In another particular exemplary embodiment, threads 112 may comprise M8×1.25 dual-start thread paired with 2.5 mm pitch bone thread. Those skilled in the art will recognize that thread configurations of other dimensions may be suitable for particular operative conditions and may thus be readily adapted by those skilled in the art. However in each case, threads on threaded head 118 of proximal portion 116 are provided a lead matching the selected pitch of external threads 112. In at least certain exemplary configurations, the lead of threads may be different than pitch because the threads are dual-start (lead). In exemplary configurations, external threads 112 of anchor portion 110 may be self-tapping or partially self-tapping. Likewise in exemplary configurations, the external surface may be roughened (e.g., to increase surface area) and/or include a coating (e.g., to encourage bone in-growth). Further in exemplary configurations, anchor portion 110 may have a tapered, elongated shape (e.g., to provide a friction fit when inserted into a generally cylindrical hole pre-formed in the patient's iliac bone). For example, in configurations in which anchor portion 110 is tapered, the outer diameter 111 of anchor portion 110 varies from a minimum outside diameter near the distal end 114 to a maximum outside diameter near the proximal portion 116. Further in exemplary configurations, the exterior surface of anchor portion 110 may include splines. Still yet further in exemplary configurations, anchor portion 110 may include a combination of features to provide fixation.

In accordance with further aspects of an embodiment, joint fusion portion 150 and anchor portion 110 may be configured to be inserted simultaneously into the patient's hip anatomy without causing undesirable damage to surrounding bone. In this regard and as noted above with respect to an exemplary configuration, external threads 112 of anchor portion 110 and internal threads 155 at the distal end 154 of joint fusion portion 150 may have substantially the same lead, such that joint fusion portion 150 and anchor portion 110 advance into a patient at substantially the same rate when simultaneously inserted. Thus, joint fusion portion 150 and anchor portion 110 exert similar pressures and/or stresses on surrounding bone to reduce the likelihood of damaging surrounding bone during insertion.

With particular reference to FIG. 3 and as noted above, anchor portion 110 preferably includes an internal cannula 117, which cannula 117 may form a channel to receive a guidewire, thus enabling guidewire placement of anchor portion 110. Cannula 117 of anchor portion 110 generally aligns with cannulated segments of other portions of the device 100, as further described below, along a longitudinal axis of anchor portion 110 and joint portion 150.

With particular reference to FIGS. 3 and 4, in an exemplary configuration anchor portion 110 includes a flange 119 positioned at the bottom of threaded head 118, which flange 119 may assist in substantially locking anchor portion 110 to joint fusion portion 150 so that they are unlikely to separate (e.g., unscrew). More particularly, when anchor portion 110 is fully joined to joint fusion portion 150 via threaded head 118 and internal threads 155, flange 119 engages the distal end 154 of joint fusion portion 150 to increase friction between anchor portion 110 and joint fusion portion 150, thus decreasing the likelihood of undesirable separation. In a particular exemplary configuration, flange 119 may include flat sections 113 (*a*) around the perimeter of flange 119, which flat sections 113 (*a*) allow for tightening of anchor portion 110 with, by way of non-limiting example, a wrench or similarly configured tool. Further and in order to further aid in placement of anchor portion 110 into the patient's iliac bone, proximal portion 116 may include a receiver slot 113 (*b*) for a shaped driver element, such as a TORX slot.

Figure 9:
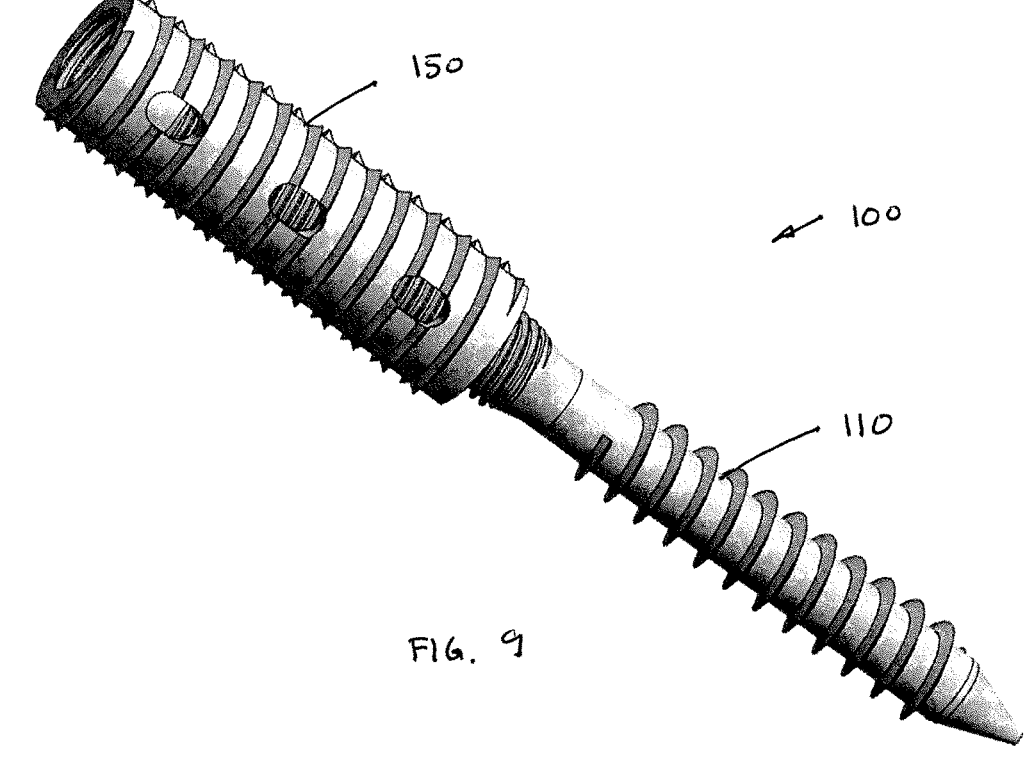
FIG. 9 is a perspective view of the implantable device of FIG. 1 having a modular configuration.
Figure 10:
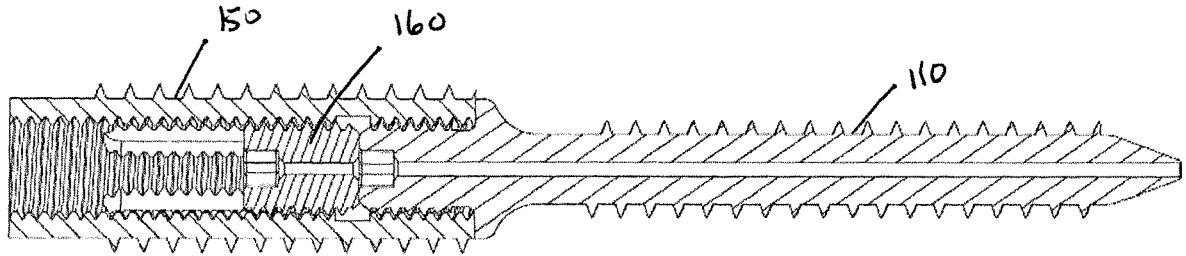
FIG. 10 is a side cross-sectional view of the implantable device of FIG. 1.

Further, in certain exemplary configurations and with particular reference to FIG. 9, coupling hardware 160, such as by way of non-limiting example a set screw, jam nut or the like, may be threaded into the threaded hollow interior of joint fusion portion 150 (e.g., via internal threads 157 mating with external threads on coupling hardware 160) configured to further reduce the likelihood of the anchor portion 110 and joint fusion portion 150 decoupling from one another. In this configuration, coupling hardware 160 thus assists in substantially locking anchor portion 110 to joint fusion portion using an additional fastener. Coupling hardware 160 threadably engages the hollow interior of joint fusion portion 150 to further engage the end of proximal portion 116 of anchor portion 110, such as by frictional engagement. In such configurations, coupling hardware 160 preferably is itself cannulated to allow use with a guidewire. Thus, frictionally engaging coupling hardware 160 in the hollow interior of joint fusion portion 150 against anchor portion 110 reduces the likelihood of undesirable separation.

As noted above, joint fusion portion 150 has a hollow interior and includes a plurality of openings or slots 158 extending through the external wall of joint fusion portion 150. In this configuration, joint fusion portion 150 may be configured to facilitate bony in-growth, such as by holding bone graft material and allowing bony in-growth through slots 158 into the hollow interior. Thus, bony in-growth through a plurality of slots 158 into the hollow interior of fusion portion 150 where fusion portion 150 is positioned across a SI joint further fuses the joint. By way of example, such bony in-growth may encourage fusion spanning a distance between the sacrum and ilium. In one example, the join fusion portion 150 may cross through an articular portion of the patient's SI joint. In another example, the joint fusion portion 150 may cross through a ligamentous portion of the patient's SI joint. In certain configurations, slots 158 may have different shapes, such as elliptical or parallelogram. Still further, joint fusion portion 150 may have surface treatments (e.g., on outer and interior surfaces) that encourage bony in-growth and attachment (such as roughened surfaces and/or surface coatings). Still yet further, the hollow interior of joint fusion portion 150 may form a cannulation canal that is configured to function with cannula 117 of anchor portion 110 to, for example, pass a guidewire through the cannula of anchor portion 110 and the cannulation canal of the joint fusion portion 150. Still further, the threads 155 on the interior of joint fusion section 150 may comprise machine threads that match the lead of outer threads on anchor portion 110 to preserve bone during placement of anchor portion 110 (e.g., when joint fusion portion 150 of device 100 has already been secured into the patient's distal iliac wing prior to placement of anchor portion 110).

Next and with particular reference to FIGS. 7 and 9 showing top and perspective views of joint fusion portion 150 device 100 may be configured to enable placement of a plurality of devices 100 within a bony portion of the patient's pelvis to provide additional support and fixation across the patient's SI joint. For example, multiple devices 100 may be used such that the anchor portions 100 are positioned within a pelvic bony portion and the respective joint fusion portions 150 are positioned adjacently across the patient's SI joint. In such a configuration, a plurality of joint fusion portions 150 and/or anchor portions 110 may be installed within a single aperture in the bony portion. For example, in a configuration in which two joint fusion portions are to be used and installed within one aperture, each joint fusion portion 150 is configured to fit within the aperture in generally close proximity to the adjacent joint fusion portion 150 (e.g., each joint portion is separated from the other joint portion by a distance that is approximately equal to or less than a diameter (e.g., major or minor) of one of the joint fusion portions 150. For example, the outer body of joint fusion portions 150 may have cut-ins 159 (scalloped sides or lobe-like) as shown in FIGS. 7 and 9, thus having a smaller diameter dimension than non-cut-in portions of the outside diameter of joint fusion portion 150. In certain exemplary configurations, cut-ins 159 may be configured to engage with a wrench to tighten joint fusion portion 150 (e.g., tighten joint fusion portion 150 to anchor portion 110), such that cut-ins 159 are substantially parallel to one another on the outer body of joint portion 150.

Figure 17:
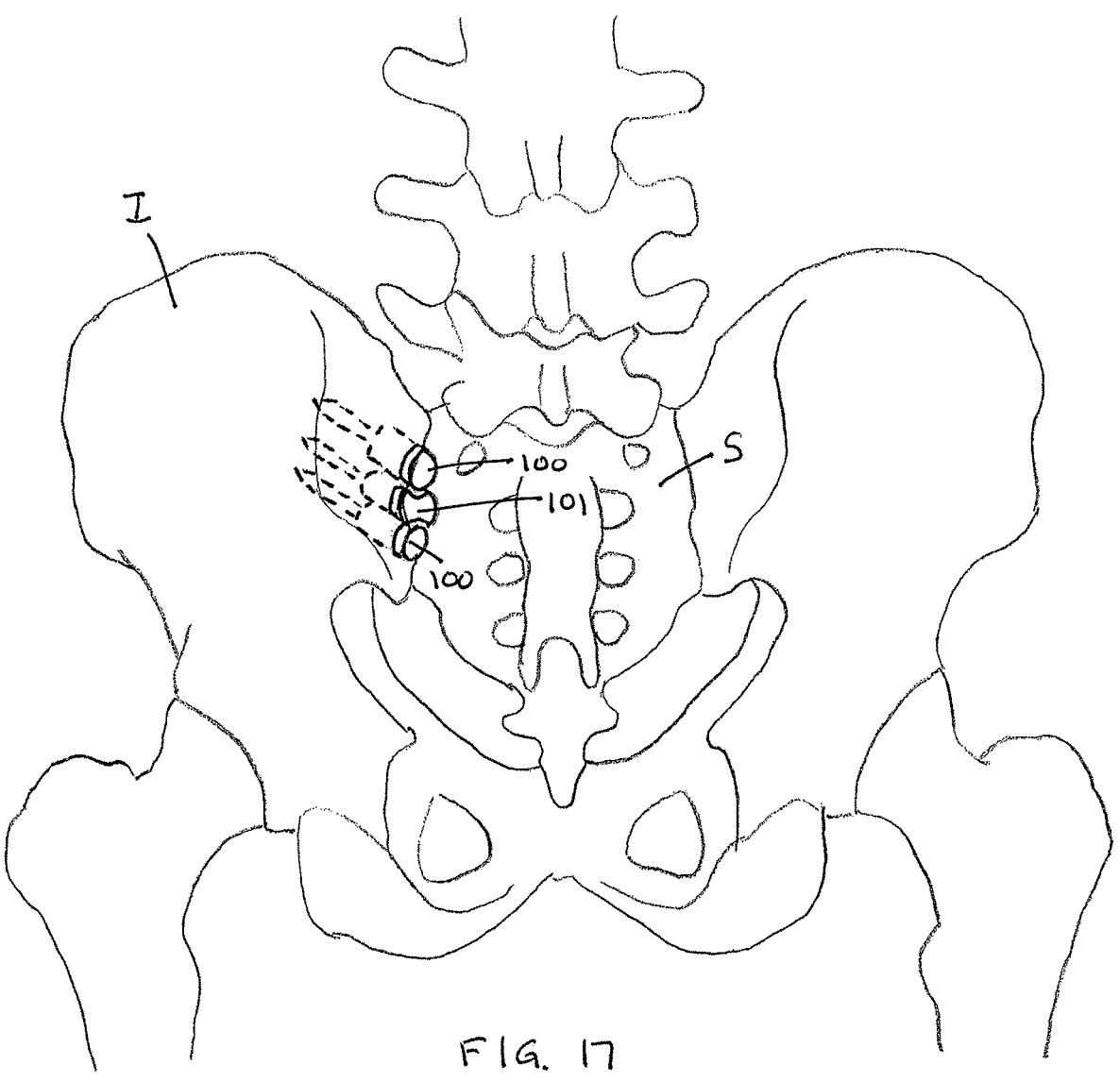
FIG. 17 is a rear schematic view of a patient's pelvis showing positioning of multiple implantable devices according to certain aspects of an embodiment of the invention.
Figure 18:
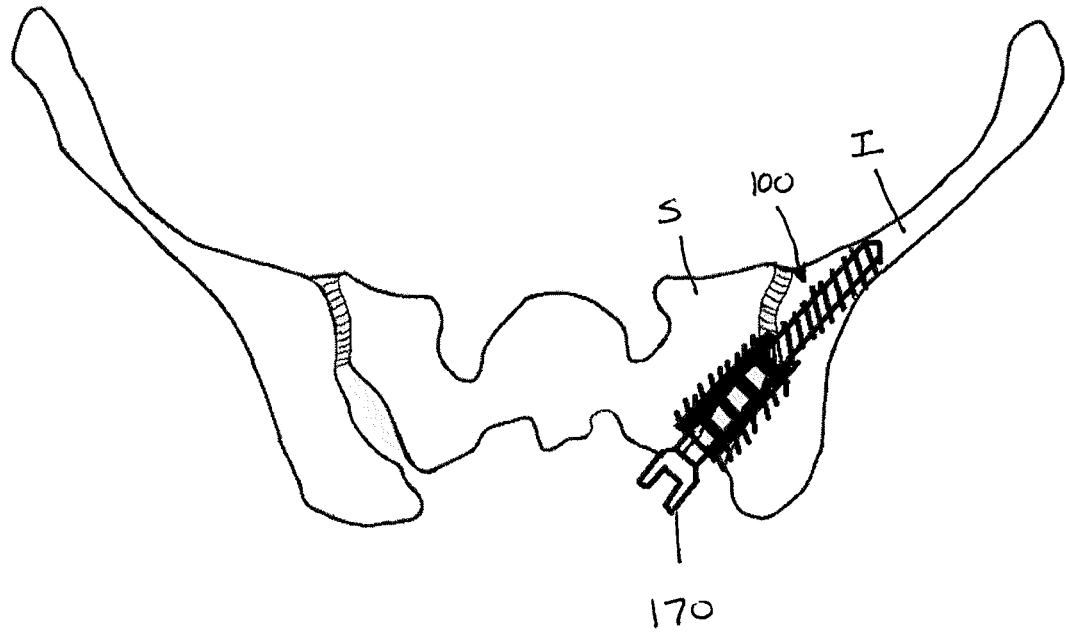
FIG. 18 is a top, sectional view of a patient's pelvis showing positioning of an implantable device according to certain aspects of an embodiment of the invention.

FIG. 17 shows a back view of a patient's pelvis with a plurality of devices 100 configured in accordance with aspects of the invention installed, and FIG. 18 shows a top, sectional view of the patient's pelvis showing one of such devices 100 extending across the patient's SI joint. With particular regard to FIG. 17, a plurality of devices 100 are installed with one of such devices (and particularly the middle device 101) having a lobe-like cross-section as discussed above with respect to FIGS. 7 and 9. The cross-section of device 101 has a major diameter Dma, which is approximately equal to an outside diameter of elliptical-like cross-sections of devices 100 (e.g., as described above). Thus, insertion (e.g., drilling and reaming) techniques are generally similar, as further described below. However, lobe-like cross-sections on middle device 101 also have a minor diameter Dmi that is smaller than the major diameter Dma. In such configurations, the major diameter Dma is generally aligned perpendicularly to the minor diameter Dmi. In certain exemplary configurations, the minor diameter Dmi is smaller compared to the major diameter Dma by a length that is inversely proportional to the distance between the lobe-like joint portion of device 101 and an adjacent joint portion of devices 100. In other words, and by way of example, a joint portion of a device 101 having lobed-like joint portions may exhibit a major diameter Dma that is significantly greater than the minor diameter Dmi (although this can be based on other factors, such as the absolute difference (|Dma−Dmi|), etc.) for devices configured to be positioned closely adjacent (e.g., d<Dma) to another joint portion. Positioning such a configuration in a bony portion may include additional steps compared to typical devices (e.g., having only cross-sections of similar elliptical- or triangular-like shapes), as further described below. In any case, and by way of example, positioning devices 101 closely adjacent to another joint fusion portion 150 can include overlapping or interdigitating outer threads of the joint fusion portions 150.

As best shown in FIG. 18, device 100 (as well as device 101 having lobe-like portions) may be configured to couple to external devices, such as spinal construct equipment. In an exemplary configuration, device 100 may include a connector 170 configured to couple to spinal construct equipment (not shown) and to device 100. For example, connector 170 may couple to the joint fusion portion 150 of device 100, while in other configurations, the connector 170 may couple to anchor portion 110 of device 100 (e.g., near the coupling of anchor portion 110 to joint portion 150). Connector 170 may be coupled using many mechanisms, including fasteners (e.g., such as those having Philips heads, flat-heads, or Torx heads), friction fitting, threads, and the like using typical hardware well known to those of ordinary skill in the art.

Components of the above-described system may be formed from a variety of biologically acceptable materials suitable for medical applications, and may comprise metals, ceramics, synthetic polymers, bone material, composites, and the like as may be selected by a practitioner to meet their particular objectives and preferences for a given application, such as to provide particularly desired characteristics such as strength, rigidity, biomechanical performance, and the like as will readily occur to those skilled in the art. Likewise, anchor portion 110 and joint portion 150 may be variously configured and dimensioned with regard to size, shape, thickness, geometry and material, again to meet a practitioner's particular objectives and preferences for a given application. For example and with particular reference to FIGS. 11-16, anchor portion 110 may be provided in varying lengths, such as by way of non-limiting example having shaft lengths of 10 mm, 15 mm, and 20 mm. In each such configuration, thread gap 153 in joint fusion portion 150 is provided at a different location to accommodate the full length of the proximal portion 116 of anchor portion 110.

As mentioned above and with particular reference to FIGS. 17 and 18, joint fusion portion 150 is particularly configured to fixate the SI joint, and more particularly is configured for placement across the SI joint, which placement serves to fix the relative positions of the patient's sacrum and ilium and allow for arthrodesis across the SI joint. During installation of device 100, particularly in those cases in which device 100 is formed as an integral unit or in those cases in which modular device 100 is installed as a fully assembled unit, the patient's SI joint forms a trajectory for device 100 into the SI joint followed by entry into the patient's iliac wing. A multi- or dual diameter reaming device and/or tap (not shown) may be used to provide simultaneous development of a hole for anchor portion 110, removal of bone from both the patient's sacrum and ilium, and insertion of device 100 with joint fusion portion 150 allowing for both fixation of equipment to the patient's pelvis and SI joint fusion.

A method is thus provided in accordance with further aspects of an embodiment of the invention for installing a device 100 in a patient's pelvis in order to particularly fuse their SI joint and provide an anchor for attachment of spinal equipment to the patient's pelvis. In that regard, such method includes positioning a patient in a prone position. Next, anesthetic is applied to at least one of the patient, generally, and locally to the patient's SI joint. In implementations in which fluoroscopy guidance is used, the method preferably includes further providing a contrast agent. The method may further include creating an incision at a location at a proximal end of the intended location of the aperture to be formed in the patient's pelvis for receiving a device 100.

Next, and in accordance with aspects of the invention, at least one aperture is formed between a sacro pelvic bony portion and an iliac bony portion of the patient's pelvis, crossing the patient's SI joint. In one example, at least one aperture crosses through an articular portion of the patient's SI joint. In another example, at least one aperture crosses through a ligamentous portion of the patient's SI joint. By way of example, forming the aperture may include identifying a desired aperture position. Forming the aperture may further include drilling a guide aperture in the desired aperture position. Still further, forming the aperture may include drilling the aperture for the anchor portion 110 at the position of the guide aperture to a desired diameter (e.g., approximately a diameter of the anchor portion 110) and having a depth into the iliac bony portion that is approximately the length of the anchor portion 110 (generally a predetermined depth). Furthermore, forming the aperture may include drilling the aperture for the joint fusion portion 150 at the position of the aperture to a desired diameter (e.g., approximately a diameter of the joint fusion portion 150) and at a distal depth that approximately crosses the SI joint. In certain configurations, forming the aperture may include reaming the aperture to a desired diameter of the anchor portion 110 and joint fusion portion 150.

The method according to aspects of the invention may further include placing the anchor portion 110 into the aperture, such as by applying force along the axis of the anchor portion 110 and/or by screwing (e.g., rotating) the anchor portion 110 within the bony portion of the patient's iliac bone. In exemplary implementations, placing the anchor portion 110 may include rotating the anchor portion 110 to a desired rotational orientation relative to external features, such as physiological markers, spinal construct equipment, etc., to facilitate attachment to spinal constructs and/or to the joint fusion portion 150.

The method according to aspects of the invention may further include placing the joint fusion portion 150 into the aperture, such as by applying force along the axis of the joint fusion portion 150 and/or by screwing (e.g., rotating) the joint fusion portion 150 within the bony portion of the patient's sacrum and across the patient's SI joint. In certain configurations, placing the joint fusion portion 150 may include coupling the joint fusion portion 150 to the anchor portion 110, such as by mechanically screwing the joint fusion portion 150 to threads of the anchor portion 110. Furthermore, coupling may include fixing additional attachment hardware (e.g., fasteners) to increase securement of the joint fusion portion 150 to the anchor portion 110.

In certain exemplary implementations, the method may include using a jig for aligning the anchor portion 110 to the aperture, aligning the joint fusion portion 150 to the anchor portion 110, etc. The method may further use other instruments, such as a chisel, bar, a drill, a saw, curette, a cutting laser, or electrosurgical instruments, or the like.

Furthermore and in accordance with still further aspects of the invention, the method may include placing bone growth material within the joint fusion portion 150. Likewise, the method may include coupling the device 100 to a spinal structure, such as (by way of non-limiting example) by attaching a connector 170 to the joint fusion portion 150 and to a spinal construct. Alternatively, coupling the device 100 to a spinal structure may include attaching the connector 170 to the anchor portion 110 and to a spinal construct.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. Thus, it should be understood, therefore, that the invention may be practiced otherwise than as specifically set forth herein.

What is claimed is:

1. A device for sacroiliac joint fusion, comprising:
  a joint portion having a first diameter, a joint portion proximal end and a joint portion distal end, a first plurality of joint portion threads on an exterior of said joint portion, a second plurality of joint portion threads on an interior of said joint portion at said joint portion distal end, and a third plurality of joint portion threads on an interior of said joint portion at said joint portion proximal end, the joint portion configured for implantation across an SI joint of a patient such that said joint portion distal end extends into an ilium of the patient from a sacrum of the patient; and
  an anchor portion having a second diameter that is less than the first diameter of the joint portion, the anchor portion including a proximal portion with external threads thereon and an anchor portion distal end with a first plurality of anchor portion threads thereon, the anchor portion extending distally from the distal end of the joint portion such that said external threads of said proximal portion engage said second plurality of joint portion threads to threadably couple said anchor portion to said joint portion, and configured for implantation into the ilium of the patient such that the entire length of the anchor portion that is distal to the joint portion is implanted within the ilium of the patient;
  wherein said joint portion further comprises an internal smooth cylindrical wall defining a gap between said second plurality of joint portion threads and said third plurality of joint portion threads, said gap configured to separate said second and third pluralities of joint portion threads.

2. The device of claim 1, wherein a lead of said first plurality of joint portion threads matches a pitch of said first plurality of anchor portion threads.

3. The device of claim 2, wherein said anchor portion further comprises a plurality of separated flat, planar outer edge portions along the exterior of said anchor portion.

4. The device of claim 2, wherein said joint portion further comprises a plurality of indented scalloped side edge portions along the exterior of said joint portion, said scalloped side edge portions configured to allow placement of a plurality of devices adjacent to each other such that joint portions of adjacent devices fit within an aperture in close proximity to each other.

5. The device of claim 1, wherein said joint portion further comprises a plurality of openings extending through a side wall of said joint portion.

6. The device of claim 1, wherein said anchor portion is threadably attached to said joint portion via said external threads of said proximal portion of said anchor portion engaging said second plurality of joint portion threads on said interior of said joint portion.

7. The device of claim 6, further comprising a set screw threadably attached to an interior of said joint portion and configured to abut a proximal end of said anchor portion, wherein said set screw threadably engages said third plurality of joint portion threads and frictionally engages said proximal end of said anchor portion to reduce likelihood of separation of said anchor portion from said joint portion.

8. The device of claim 6, further comprising a shaped drive element receiver at a proximal end of said anchor portion.

9. The device of claim 1, further comprising a cannula extending through said anchor portion from said anchor portion distal end to said joint portion proximal end.

* * * * *